United States Patent [19]

Groeneweg et al.

[11] Patent Number: 4,902,809

[45] Date of Patent: Feb. 20, 1990

[54] METHOD FOR MAKING N-SUBSTITUTED NITROPHTHALIMIDES

[75] Inventors: Peter G. Groeneweg, Ancaster, Canada; Roy R. Odle, Schuylerville, N.Y.

[73] Assignee: General Electric Company, Pittsfield, Mass.

[21] Appl. No.: 917,926

[22] Filed: Oct. 10, 1986

Related U.S. Application Data

[63] Continuation of Ser. No. 559,616, Dec. 8, 1983, abandoned.

[51] Int. Cl.⁴ .......................................... C07D 209/48
[52] U.S. Cl. ..................................................... 548/481
[58] Field of Search ................................. 548/480, 481

[56] References Cited

U.S. PATENT DOCUMENTS

| | | | |
|---|---|---|---|
| 3,415,876 | 12/1968 | Boonstra et al. | 260/515 |
| 3,868,389 | 2/1975 | Takekoshi | 260/326 N |
| 3,920,697 | 11/1975 | Takekoshi | 260/326 N |
| 3,933,852 | 1/1976 | Cook et al. | 260/326 N |
| 3,981,933 | 9/1976 | Cook et al. | 260/645 |
| 4,020,089 | 4/1977 | Markezich | 260/326 R |
| 4,036,838 | 7/1977 | Vogel et al. | 260/251 R |
| 4,064,147 | 12/1977 | Thelen et al. | 260/369 |
| 4,112,005 | 9/1978 | Thiem et al. | 568/706 |
| 4,599,429 | 7/1986 | Odle | 548/487 |

FOREIGN PATENT DOCUMENTS

| | | |
|---|---|---|
| 0108604 | 5/1984 | European Pat. Off. . |
| 2270247 | 12/1975 | France . |
| 329367 | 6/1958 | Switzerland . |
| 635635 | 4/1950 | United Kingdom . |

OTHER PUBLICATIONS

Hughes et al., "Kinetics and Mechanism of Aromatic Nitration Part II", pp. 2400–2440, 1949.

Shofield, K., "Aromatic Nitration", Cambridge University Press, pp. 23–43, 1980.

Astle, M. J., "Industrial Organic Nitrogen Compounds", Reinhold Publishing Corp., pp. 314–344, 1961, p. 459, 1943.

Houben-Weyl, Methoden der Organischen Chemi, vol. X/1, part 1, 1971, George Thieme Verlag (Stuttgart, DE), pp. 622–623.

Gordon et al, "The Chemist's Companion", John Wiley and Sons, p. 152 (1972).

Blatt, A. H., ed., "Organic Synthesis", Collective vol. 2, John Wiley and Sons, p. 459 (1943).

*Methods of Organic Chemistry* (Houben-Weyl), vol. X/1, Nitrogen Compounds I, Part 1, Fourth Ed., pp. 622–624.

C. Noller, Chemistry of Organic Compounds, Second Edition, W. B. Saunders Co., Philadelphia, QD253N65.

Gordon et al, The Chemist's Companion, John Wiley and Sons, p. 152 (1972).

Albright et al, Ed., Industrial and Laboratory Nitrations, ACS, pp. 48, 49 (1976).

Blatt, A. H., Ed., Organic Synthesis, Coll. vol. 2, John Wiley and Sons, p. 459 (1943).

March, Jerry, Advanced Organic Chemistry, second edition, McGraw-Hill, NY (1977), pp. 388–389, 474–476.

*Primary Examiner*—Mary E. Ceperley
*Attorney, Agent, or Firm*—Bernard, Rothwell & Brown

[57] ABSTRACT

A process for preparing N-alkyl substituted nitrophthalimide by the nitration of N-alkyl substituted phthalimide using only nitric acid, said nitric acid having a concentration of at least about 95%, and then recovering N-alkyl nitrophthalimide from the nitric acid solution.

10 Claims, No Drawings

METHOD FOR MAKING N-SUBSTITUTED NITROPHTHALIMIDES

This is a continuation of application Ser. No. 559,616 filed 12/8/83, now abandoned.

The present invention is concerned with a process for making nitrated derivatives of N-alkylphthalimide, wherein the alkyl group contains from 1 to 8 carbon atoms, preferably from 1 to 4 carbon atoms. More specifically, the invention is concerned with a process for making N-alkyl nitrophthalimides of the formula

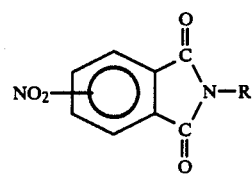

wherein R is an alkyl group having from 1 to 8, preferably from 1 to 4, carbon atoms, which comprises forming a solution of N-alkylphthalimide in a solvent composed of at least about 95%, preferably at least about 97.5%, concentrated nitric acid within a temperature range of from about $-20°$ C. to the boiling point of nitric acid, preferably from about 10° C. to about 70° C., most preferably from about 20° C. to about 60° C. and recovering the nitrated products by known methods to obtain the desired nitro derivatives of the N-alkylphthalimides.

Alternative methods for preparing N-alkyl nitrophthalimides are constantly being sought as these compounds are especially useful as basic starting reactants for making a variety of organic dianhydrides and polyimides as shown by Heath et al, U.S. Pat. Nos. 3,879,428; 3,874,867 and 3,787,475, all assigned to the same assignee as the present invention. Prior to the present invention one method for preparing N-substituted nitrophthalimides involved effecting a reaction between nitrophthalic anhydride and an organic isocyanate in the presence of an alkali carbonate catalyst. See e.g. Takekoshi, U.S. Pat. No. 3,868,389. More recently another method for the preparation of N-alkyl nitrophthalimides was disclosed by Cook et al, U.S. Pat. No. 3,933,852, wherein a solution of N-alkylphthalimide in a solvent composed of 98-103% concentrated sulfuric acid is prepared, then said solution is admixed with a 98-100% concentrated nitric acid within a temperature range of 60° to 80° C. and thereafter the reaction products are recovered by methylene chloride extraction. This process produces product yields of about 90% comprising a mixture of about 94% 4-nitro-N-methylphthalimide, about 5% 3-nitro-N-methylphthalimide and about 1% unreacted N-methylphthalimide.

Unexpectedly, it has now been discovered that N-alkylphthalimide may be nitrated to form N-alkyl nitrophthalimides in an all nitric acid nitration process. This process eliminates the additional requirement and expense of sulfuric acid, is effective over a wider range of temperatures and provides greater yields. Furthermore, this new process is considered safer and less costly than prior processes, particularly in the event of a cooling failure and/or a runaway reaction.

Finally, recovery of the reaction products may be by any known extraction method and is easier since removal of sulfuric acid is no longer a consideration. Instead the product of the present invention is recovered directly from the nitric acid.

SUMMARY

According to this invention there is provided a new process for the preparation of N-alkyl nitrophthalimides from N-alkylphthalimides comprising (1) mixing the N-alkylphthalimide, wherein the alkyl is a $C_1$ to $C_8$, preferably a $C_1$ to $C_4$, hydrocarbon, with at least about 95%, preferably at least about 97.5% concentrated nitric acid; (2) reacting the mixture within a temperature range of about $-20°$ C. to the boiling point of nitric acid, preferably from about 10° C. to about 70° C., most preferably from about 20° C. to about 60° C.; (3) allowing the reaction to run to produce the nitrated derivatives and (4) thereafter recovering the nitrated products by known methods to obtain a mixture composed essentially of the 3- and 4-isomers of N-alkyl nitrophthalimide.

The weight ratio of the starting reactants, nitric acid to N-alkylphthalimide may vary widely. Generally said ratio is from about 0.4 to about 50, preferably from about 5 to about 30, most preferably from about 9 to about 15.

DETAILED DESCRIPTION OF THE INVENTION

The nitric acid useful for the nitration process disclosed herein should have a concentration of at least about 95% and is preferably within the range of from about 97.5 to about 100% concentration. Nitric acids of lower concentration are useful for the all nitric acid nitration process; however, the use of such concentrations results in processes which are too slow to be cost effective. Nitric acids of such concentrations are available commercially or may be prepared by known concentrating methods from more widely available commercial nitric acid of 60 to 67% concentration.

The amount of concentrated nitric acid used should be at least of the stoichiometric amount necessary to attach one $NO_2$ group on the aromatic nucleus of the N-alkylphthalimide. Generally, the weight ratio of nitric acid to the N-alkylphthalimide should be from about 0.4 to about 50, preferably from about 5 to about 30, most preferably from about 9 to about 15. Obviously, lower or higher amounts of nitric acid may be used in the process of the present invention, however, lower amounts of nitric acid result in poor yields and too slow a reaction rate as to be cost effective, whereas higher amounts of nitric acid may result in unnecessary spoiling of concentrated nitric acid and increased cost for such acid and its recycling.

The N-alkylphthalimides suitable for the nitration process disclosed herein are those of the formula I, above, wherein R is a $C_1$ to $C_8$, preferably $C_1$ to $C_4$, hydrocarbon. They may be prepared by effecting reaction between an alkylamine and phthalic anhydride as taught by Markezich in U.S. Pat. No. 4,020,089, incorporated herein by reference. The N-alkylphthalimide may be added to the reactor in any suitable form, e.g. powder, flake, etc. This process is particularly suitable for the nitration of N-alkylphthalimide wherein the alkyl group is methyl, ethyl, n-propyl, i-propyl or n-butyl.

The process of the present invention comprises mixing together the concentrated nitric acid and the N-alkylphthalimide in a reactor or reactors preferably equipped with a stirrer or agitating means and means for heating or cooling the reactor. The reactor(s) may be such as to allow for either batch or continuous processing.

Specific variations in the design of the process systems employable to practice the present invention are known to those skilled in the art. For example, it is possible to use one or more reactors in series or in parallel which operate in the plug flow mode with or without radial mixing and with or without heating or cooling. Alternatively, it is possible to use one or more reactors in series or in parallel which operate in the back mixing mode, again with or without heating and cooling and operating in a batch or continuous mode. Finally, it is also possible to use a combination of reactors with features of both the foregoing.

The mode of mixing and sequence of addition of reactants is not critical to the present invention. Feed of the reactants may either be into the first reactor or be portioned among the reactors if more than one reactor is used, or they may be entered at different locations of the reactor or reactors. Further, the reactants may be pre-mixed before entering the reaction process or they may be fed separately. It is also possible that one or both reactants are brought to the desired reaction temperature prior to mixing or entering the reactor.

Generally, the reaction temperature should fall within the range of from about −20° C. to the boiling point of nitric acid, preferably from about 10° C. to about 70° C., most preferably from about 20° C. to about 60° C. More specifically, the actual temperature to be employed is dependent upon the desired rate of reaction and the desired end products. In general, the lower the temperature the slower the reaction and the greater the ratio of the 4-isomer to 3-isomer formed in the products. Conversely, with the higher temperatures, the reaction rate is increased and the ratio of 4-isomer to 3-isomer is smaller.

For the purpose of this specification and the appended claims, the "boiling point of nitric acid" is defined as the temperature at which the specific nitric acid used, under the pressure employed, boils. This definition is necessitated by the fact that nitric acids of less then 100% concentration have a higher boiling point than 100% concentrated nitric acid and that the boiling point of nitric acid may be elevated by raising the pressure under which the reaction takes place above atmosphere. Such instances are clearly intended to be within the full scope of the present invention as set forth in this specification and claimed by the appended claims.

It should also be noted that temperatures outside the range of temperatures disclosed above may be employed with the present process. However, lower temperatures result in a reaction rate which is too slow to be cost effective, whereas higher temperatures require operation at above atmospheric pressure to prevent boiling and subsequent loss of nitric acid.

While the temperature at which the reaction is run has a very significant impact on reaction rate, the specific reactants used and the ratio of reactants in the reaction mix also greatly influence the reaction rate. With respect to the latter, the higher the concentration of the nitric acid in the initial mix or as added during continuous processing the faster the reaction rate. Further, the specific alkyl group on the N-alkylphthalimide is found to influence reaction rate. Generally, it has been found that the more electron donating alkyl groups, especially for example isopropyl, influence a comparatively faster reaction than for example, the methyl group. Finally, with respect to the ratio of the reactant mix, it is found that the rate of reaction increases as the ratio of nitric acid to N-alkylphthalimide increases. The most dramatic reaction rate increase, in this respect, being noted as the reactant ratio approaches about 10.

Thus by varying any one or all of the foregoing, one may significantly increase or decrease the time for which the reaction should run to obtain optimum yield. In general, with a reaction run at a temperature within the preferred range, e.g. 20°–60° C., up to about 90% or greater yield may be obtained within three hours. Optionally, these yields may be increased further by allowing the reaction mix to stand for a period of time prior to separation.

The pressure range under which this process operates may vary from vacuum to above atmospheric pressure. Depending on the type of reactor or reactors employed, they may preferentially operate under slight vacuum for process and safety reasons. Otherwise, the process is generally run at about atmospheric pressure.

The desired reaction products of this invention are comprised primarily of the 3- and 4-isomers of the respective N-alkyl nitrophthalimide. As mentioned above, the specific ratio of the 3- and 4-isomers is largely dependent upon the temperature at which the reaction is run. For example, the ratio of 4- to 3-isomer may vary from about 16:1 at about 60° C. to about 26:1 at about 15° C. The weight ratio of starting reactants may also have a slight influence on the isomer ratio.

The reaction products themselves may be recovered from the reaction mix by any of the known methods for recovery of nitrated products. Exemplary of the methods available include; extraction; spray drying; precipitation and drying and the like. Recovered unreacted N-alkylphthalimide may be reused and the spoiled or used nitric acid may be recycled by known methods for reuse.

In order that those skilled in the art may better understand how the present invention may be practiced, the following examples are given by way of illustration and not by way of limitation.

DESCRIPTION OF THE PREFERRED EMBODIMENTS

Generally, reaction products in Examples 7–26 were analyzed by High Pressure Liquid Chromatography (HPLC) wherein 50 μl aliquots were quenched into 3 mls of an aqueous phase and 2 mls of an organic phase: the former comprising 0.1M tetramethylammonium chloride in water and 1.0% methanol and the latter comprising 10% methanol in acetonitrile. The samples were analyzed at 280 nm on a duPont ODS-RP column using 1.5 ml/min of mobile phase. A solvent gradient of 12–40% organic phase was programed using a linear gradient over 20 minutes.

COMPARATIVE EXAMPLE CE1

45.6 parts by wt. N-methylphthalimide is added to 100 parts by wt. of 100% Sulfuric Acid. The solution is heated to 70° C. and thereafter 22 parts by wt. of 98.1% nitric acid is added to the solution. This nitration process produces a yield of 89.3% comprising a mixture of the 3- and 4-isomers of N-alkyl nitrophthalimide.

A comparison of Comparative Example CE1 and the examples of this invention below show the improved yields obtained by the all nitric acid nitration process.

EXAMPLE 1

7.98 parts by wt. N-methylphthalimide is dissolved in 100 parts by wt. of 99.2% nitric acid with an initial temperature of 20° C. The reaction is allowed to run for approximately 24 hours and produces a 97% yield of a mixture of 4- and 3-nitro-N-methylphthalimide.

EXAMPLE 2

2.17 parts by wt. N-methylphthalimide is dissolved in 100 parts by wt. of 99.2% nitric acid with an initial temperature of 20° C. The reaction mixture is heated to 25° C. and held at 25° C. for 24 hours. The reaction produces a 99.9% yield of a mixture of 4- and 3-nitro-N-methylphthalimide.

EXAMPLE 3

3.95 parts by wt. N-methylphthalimide is dissolved in 100 parts by wt. of 98.8% nitric acid with an initial temperature of 20° C. The reaction mixture is heated to 25° C. and held at 25° C. for approximately 4 hours. The reaction mixture is cooled to room temperature and produces a 98% yield of a mixture of 4- and 3-nitro-N-methylphthalimide.

EXAMPLE 4

10 parts by wt. N-methylphthalimide is dissolved in 100 parts by wt. 98% nitric acid at an initial temperature of 20° C. The reaction mixture is heated to 25° C. and held at 25° C. for approximately 24 hours. The reaction products are then extracted to produce a 99.5% yield of a mixture of 4- and 3-nitro-N-methylphthalimide.

EXAMPLE 5

10 parts by wt. N-methylphthalimide is dissolved in 100 parts by wt. of 98% nitric acid with an initial temperature of 20° C. The reaction mixture is heated to 45° C. and held at 45° C. for 3 hours. The reaction mixture is then cooled to room temperature to produce a mixture of 4- and 3-nitro-N-methylphthalimide containing 0.125% of a phenolic by-product and no starting material (greater than 96.5% yield).

EXAMPLE 6

10 parts by wt. N-methylphthalimide is dissolved in 100 parts by wt. of 98% nitric acid with an initial temperature of 21° C. The reaction mixture is heated to 35° C. and held at 35° C. for 3 hours. The reaction mixture is then cooled to room temperature to produce a mixture of 4- and 3-nitro-N-methylphthalimide containing 1.10% of a phenolic by-product and 1.6% unreacted starting material (greater than 96.5% yield).

EXAMPLES 7-11

10 parts by wt. each of N-methylphthalimide, N-ethylphthalimide, N-isopropylphthalimide, N-n-propylphthalimide and N-n-butylphthalimide are added to individual solutions of 100 parts by wt. 99% nitric acid which has previously been brought to a temperature of 40° C. The reaction mixture is maintained at 40° C. to produce yields over time as shown in Table 1. Table 1 also indicates the half lives for the various reactions.

TABLE 1

| $R^a$ | $t_{\frac{1}{2}}^b$ | % Yield/Time (min.) |
|---|---|---|
| —CH$_3$ | 31 | 89/180 min. |
| —CH$_2$CH$_3$ | 16 | 95$^c$/180 |

TABLE 1-continued

| $R^a$ | $t_{\frac{1}{2}}^b$ | % Yield/Time (min.) |
|---|---|---|
| —CH(CH$_3$)$_2$ | 11 | 91/120 |
| —CH$_2$CH$_2$CH$_3$ | 19 | 83/160 |
| —CH$_2$CH$_2$CH$_2$CH$_3$ | 26 | 64/180 |

$^a$R represents the alkyl group present on the N—alkylphthalimide reactant
$^b$time for the first 50% of starting material to react in minutes
$^c$% yield is based on disappearance of starting material.

EXAMPLES 12-15

A series of reactions are conducted by adding 20 parts by wt. N-methylphthalimide to 100 parts by wt. 99% nitric acid which has been elevated in temperature to 40° C. The temperature at which the reaction is run is varied, as shown in Table 1, to demonstrate its effect on reaction rate, represented by $t_{\frac{1}{2}}$.

TABLE 2

| Example | wt. ratio$^a$ | Temp. °C. | $t_{\frac{1}{2}}^b$ |
|---|---|---|---|
| 12 | 5/1 | 15 | 643 |
| 13 | 5/1 | 27 | 152 |
| 14 | 5/1 | 40 | 52.6 |
| 15 | 5/1 | 60 | 27.3 |

$^a$wt. ratio of HNO$_3$ to N—alkylphthalimide
$^b$same as in Table 1.

The half-lives for the reactions in each of Examples 12-15 are presented in Table 2. Table 2 clearly shows that the rate of reaction is greatly influenced by the temperature at which they are run.

EXAMPLES 16-19

A series of reactions are conducted by adding 20, 10, 6.67 and 5 parts by wt. of N-methylphthalimide to 100 parts by wt. of 99% nitric acid and reacting at a temperature of 27° C. The half-lives for these reactions are shown in Table 3. Table 3 demonstrates the effect of the weight ratio of starting reactants on reaction rate.

TABLE 3

| Example | wt. ratio$^a$ | $t_{\frac{1}{2}}^b$ |
|---|---|---|
| 16 | 5/1 | 152 |
| 17 | 10/1 | 22 |
| 18 | 15/1 | 21 |
| 19 | 20/1 | 14.3 |

EXAMPLES 20-21

Examples 20 and 21 are prepared by adding 20 parts by weight N-methylphthalimide to 100 parts by wt. nitric acid of 96 and 99% concentration, respectively, at 60° C. The resultant reaction half-lives are shown in Table 4. Table 4 demonstrates the impact of nitric acid concentration on reaction rate.

TABLE 4

| Example | Conc. HNO$_3$ | $t_{\frac{1}{2}}$ |
|---|---|---|
| 20 | 99 | 27.3 |
| 21 | 96 | 380 |

EXAMPLES 21-24

A series of examples are conducted by adding 10 parts N-methylphthalimide to 100 parts by wt. 99% nitric acid at various temperatures to determine its influence on the isomer ratio of the alkyl nitrophthalimides formed. The results, presented in Table 5, clearly demonstrate the impact of temperature on isomer ratio in the products formed.

TABLE 5

| Example | Temp. °C. | Conc. HNO₃ | wt. ratio | 4-NPI/3-NPI |
|---------|-----------|------------|-----------|-------------|
| 22 | 27 | 99 | 10/1 | 22 |
| 23 | 40 | 99 | 10/1 | 20 |
| 24 | 60 | 99 | 10/1 | 15 |

EXAMPLE 26

20 parts by wt. N-methylphthalimide is added to 100 parts by wt. of 99.6% nitric acid at a temperature of 15° C. The reaction is allowed to run and produces a mixture of 3- and 4-isomers of N-methyl nitrophthalimide, illustrating the utility of high concentration nitric acid.

Obviously, other modifications and variations of the present invention are possible in light of the above teachings. It is, therefore, to be understood that changes may be made in the particular embodiments of the invention described which are within the full intended scope of the invention as defined by the appended claims.

We claim:

1. A process for producing a mixture which consists essentially of N-alkyl-3-nitrophthalimide and N-alkyl-4-nitrophthalimide, which consists essentially of (1) mixing an N-alkylphthalimide with a nitrating reagent which consists essentially of nitric acid having a concentration of at least about 95%, (2) reacting the mixture within a temperature range of from about −20° C. to the boiling point of nitric acid and (3) thereafter recovering the N-alkyl-3-nitrophthalimide and the N-alkyl-4-nitrophthalimide.

2. The process of claim 1 wherein the nitric acid is of from about 97.5 to 100% concentration.

3. The process of claim 1 wherein the weight ratio of nitric acid to N-alkylphthalimide is from about 0.4 to about 50.

4. The process of claim 1 wherein the weight ratio of nitric acid to N-alkylphthalimide is from about 5 to about 30.

5. The process of claim 1 wherein the weight ratio of nitric acid to N-alkylphthalimide is from about 9 to about 15.

6. The process of claim 1 wherein the temperature range is from about 10° C. to about 70° C.

7. The process of claim 1 wherein the temperature range is from about 20° C. to about 60° C.

8. The process of claim 1 wherein the alkyl group of the N-alkylphthalimide has 1 to 4 carbon atoms.

9. The process of claim 1 wherein the N-alkylphthalimide is selected from the group consisting of N-methylphthalimide, N-ethylphthalimide, N-isopropylphthalimide, N-n-propylphthalide and N-n-butylphthalimide.

10. The process of claim 9 wherein the N-alkylphthalimide is N-methylphthalimide.

* * * * *